(12) United States Patent
Treynor et al.

(10) Patent No.: US 8,048,642 B2
(45) Date of Patent: Nov. 1, 2011

(54) HEME CHOLINE ESTERS AND USES THEREOF

(75) Inventors: Thomas Pirrie Treynor, Clifton Park, NY (US); Anup Sood, Clifton Park, NY (US); Sean Richard Dinn, Delmar, NY (US)

(73) Assignee: General Electric Company, Niskayuna, NY (US)

( * ) Notice: Subject to any disclaimer, the term of this patent is extended or adjusted under 35 U.S.C. 154(b) by 986 days.

(21) Appl. No.: 11/958,671

(22) Filed: Dec. 18, 2007

(65) Prior Publication Data

US 2009/0155829 A1 Jun. 18, 2009

(51) Int. Cl.
*G01N 33/53* (2006.01)
*C12Q 1/44* (2006.01)
*C12Q 1/28* (2006.01)
*C12N 9/08* (2006.01)
*C12N 9/18* (2006.01)
*C07D 487/22* (2006.01)

(52) U.S. Cl. ........... 435/7.72; 435/7.91; 435/7.92; 435/19; 435/28; 435/192; 435/197; 540/145

(58) Field of Classification Search ............ 435/7.72, 435/7.91, 7.92, 19, 28, 192, 197; 540/145
See application file for complete search history.

(56) References Cited

U.S. PATENT DOCUMENTS

| 4,340,668 A | 7/1982 | Hornby et al. |
| 4,695,539 A | 9/1987 | Sakata et al. |
| 2007/0161055 A1* | 7/2007 | Corry et al. ............ 435/7.5 |

FOREIGN PATENT DOCUMENTS

WO 2006133016 12/2006

OTHER PUBLICATIONS

Dinello et al., "Substituted Hemins as Probes for Structure-Function Relationships in Horseradish Peroxides", The Journal of Biological Chemistry, vol. 256, No. 13, Issue Jul. 10, pp. 6902-6912, 1981.
Boerakker etal., "Aggregation Behavior of Giant Amphiphiles Prepared by Cofactor Reconstitution", Chem. Eur. J., 2006, 12, 1671-6080.
Zimmerman et al., "Anisotropic Orientation of Horesradish Peroxidase by Reconstitution on a Thiol-Modified Gold Electrode", Chem. Eur. J., 2000, 6, No. 4, pp. 592-599.
Ryabov et al., "Electrochemically and Catalytically Active Reconstituted Horseradish Peroxidase with Ferrocene-Modified Hemin and an Artificial Binding Site", Chem. Eur. J., 1999, 5, No. 3, pp. 961-967.
Asakura et al., "Studies on Cytochrome c Peroxidase", The Journal of Biological Chemistry, vol. 244, No. 17, Issue of Sep. 10, pp. 4573-4579, 1969.
Ziemys et al., "Inhibition of Heme Peroxidase During Phenol Derivatives Oxidation, Possible Molecular Cloaking of the Active Center", Int. J. Mol. Sci., 2005, 6, 245-256.

* cited by examiner

*Primary Examiner* — Rosanne Kosson
(74) *Attorney, Agent, or Firm* — Eileen W. Gallagher

(57) ABSTRACT

Methods of activating an apo-peroxidase are provided. The methods include the steps of providing a solution comprising an apo-peroxidase and a heme choline ester, hydrolyzing the heme choline ester with a choline esterase, and converting the apo-peroxidase to active peroxidase. The methods disclosed herein also provide for detecting the presence of an analyte in a sample. The methods include providing a binder capable of specifically binding the analyte wherein the binder is attached to a solid surface, applying the sample to the solid surface under conditions that permit binder-analyte binding, adding a choline esterase-conjugated binder that binds to the analyte, adding an apo-peroxidase, a heme choline ester, a peroxide, and a peroxide-activated signal generator, and detecting the signal produced by the peroxide-activated signal generator. An associated kit and components are also provided.

16 Claims, No Drawings

HEME CHOLINE ESTERS AND USES THEREOF

BACKGROUND OF THE INVENTION

Single-stage enzyme-linked immunosorbent assays (ELISA) are commonly used for the qualitative or quantitative determination of an analyte. In this process an analyte is affixed to a surface and an antibody, specific for the analyte, is added. The antibody is covalently linked to an enzyme or can itself be detected by a secondary antibody or streptavidin or avidin, which is linked to an enzyme through bioconjugation. An enzymatic substrate is then added to produce a signal, such as color change, fluorescence or luminescence, which indicates the quantity of analyte in the sample. Since a single enzyme reacts with more than one enzymatic substrate, the signal is amplified and thereby increases the sensitivity of the analysis.

Successive enzymatic reactions can also be employed to increase the amplification effect. A first enzyme is used to generate multiple copies of a second enzyme, which in turn produce multiple copies of a detectable species such as an optical agent, a fluorescent dye, or a luminescent agent. In this manner signal amplification is increased through the use of coupled enzymatic reactions.

BRIEF SUMMARY OF THE INVENTION

Methods of activating an apo-peroxidase are provided. The methods include the steps of providing a solution comprising an apo-peroxidase and a heme choline ester, hydrolyzing the heme choline ester with a choline esterase, and converting the apo-peroxidase to active peroxidase.

In another aspect, provided herein are methods of detecting the presence of an analyte in a sample. The methods include providing a capture-binder attached to a solid surface or that may be attached to a solid surface, applying the sample to the solid surface under conditions that permit capture-binder to bind analyte present in the sample, adding a choline esterase-conjugated binder that binds to the analyte, adding an apo-peroxidase, a heme choline ester, a peroxide, and a peroxide activated signal generator, and detecting the signal produced by the peroxide-activated signal generator In some embodiments the detection steps comprises determining the optical density, fluorescent intensity, or luminosity of the signal generator associated with bound analyte. The method may further include the step of correlating the optical density, fluorescent intensity or luminosity of the signal generator associated with bound analyte to the concentration of the analyte in the sample.

Kits for detecting an analyte in a sample are provided. The kits include a capture-binder that specifically binds to the analyte adhered to a solid surface, a heme choline ester, and a choline esterase-conjugated binder (label-binder) that specifically binds to the analyte.

Compositions comprising the compound of formula I are also provided.

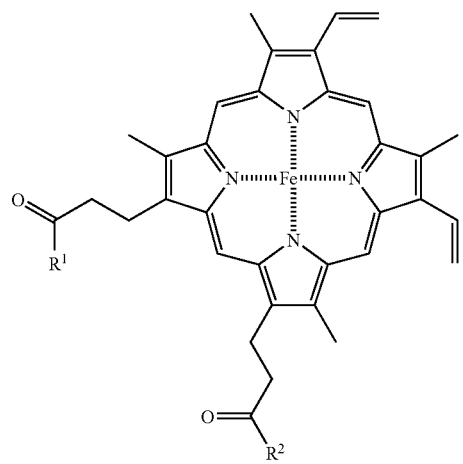

I wherein $R^1$ and $R^2$ are choline or hydroxyl; or $R^1$ and $R^2$ are choline;

with the proviso that $R^1$ and $R^2$ are not both hydroxyl.

DETAILED DESCRIPTION OF THE INVENTION

To more clearly and concisely describe and point out the subject matter of the claimed invention, the following definitions are provided for specific terms, which are used in the following description and the appended claims.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein, the term "analyte" refers to the component of a sample that may be detected when present in a sample, such as a biological sample. Representative analytes may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, and haptens.

As used herein, the term "blocking" refers to the inhibition of enzymatic activity due to the chemical modification of a reactive agent or cofactor. As applied to "blocked heme" the heme is modified in such a way to inactivate it as a cofactor for heme peroxidase.

As used herein, the term "choline esterase" refers to those enzymes that act on a variety of choline esters to hydrolyze an acylcholine forming choline and a carboxylate and is commonly referred to as choline esterase II (unspecific) and is classified according to the Enzyme Commission list of enzyme under EC number 3.1.1.8. It does not include acetylcholine esterase, which hydrolyzes acetylcholine forming choline and acetate and is commonly referred to as choline esterase I. Examples of choline esterases of class II include acylcholine acylhydrolase, benzoylcholine esterase, butyrocholine esterase, choline esterase, butyrylcholine esterase, propionylcholine esterase, pseudocholine esterase, or serum choline esterase.

As used herein, the term "heme peroxidase" generally refers to donor:hydrogen-peroxide oxidoreductases that contain heme as a cofactor. Heme peroxidases useful in the present invention include heme myeloperoxidase; lactoperoxidase; verdoperoxidase; guaiacol peroxidase; thiocyanate peroxidase; eosinophil peroxidase; Japanese radish peroxidase; horseradish peroxidase (HRP); soybean peroxidase; extensin peroxidase; heme peroxidase; MPO; oxyperoxidase; protoheme peroxidase; pyrocatechol peroxidase; scopoletin peroxidase, or cytochrome-c peroxidase.

As used herein, the term "peroxides" refers to agents capable of oxidizing other compounds upon catalysis with a peroxidase. Representative peroxides include, but are not limited to, hydrogen peroxide, alkylperoxide, polyolperoxide, and urea peroxide.

As used herein, the phrase "peroxide-activated signal generator" refers to agents capable of reacting with peroxides in the presence of a peroxidase to develop a detectable signal that indicates the presence of a target analyte that is detectable by visual or instrumental means (e.g., spectrometry, colorimetry, spectroscopy, fluorimetry, luminometry or visual inspection). Representative peroxide-sensitive signal generators that may be used with peroxidase include but are not limited to 3,3',5,5'-tetramethylbenzidine (TMB), aminophthalhydrazides, acridans, acridinium esters, dioxetanes, luminol, 2,2'-azinodi(3-ethylbenzthiazoline sulfonic acid) (ABTS), 3,3'-diaminobenzidine (DAB), labeled tyramides, labeled phenols and 3-amino-9-ethylcarbzole (AEC).

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (Ka) for the target no lower than about $10^5$ $M^{-1}$ under ambient conditions such as a pH of about 6 to about 8 and temperature ranging from about 0° C. to about 37° C.

Provided herein are reagents and methods applicable in analytical, diagnostic, or prognostic applications such as analyte detection, histochemistry, immunohistochemistry, or immunofluorescence. In some embodiments, the methods disclosed herein may be used in histochemistry, immunostaining, immunohistochemistry, immunoassays, or immunofluorescence.

Also provided are methods that increase detection sensitivity using a two-enzyme cascade amplification scheme using a blocked heme ester, an choline esterase, and an apoperoxidase that is activated by its association with the unblocked heme. The resultant active peroxidase may be used in any peroxidase-activated detection methods such as immunoassays, detection of oligonucleotides, and nucleic acid hybridization techniques.

Two-Stage Amplification

In one aspect, the methods provide two-stage amplification schemes. In the first stage, enzyme that is associated with the analyte-specific binder unblocks multiple blocked heme esters to permit heme biding to the apo-peroxidase thereby converting apo-peroxidase to active peroxidase. The second stage occurs when the active peroxidase develops signal upon interaction with a peroxide-activated signal generator. By coupling analyte recognition to a mechanism for activating heme peroxidase in situ, analyte detection and recognition sensitivity is improved in three ways: by increasing the number of heme peroxidase per molecular recognition event, by using heme peroxidase in a solution versus bound to a substrate thereby improving on chemical kinetics, and by increasing detection time suitable for signal integration. Alternatively, sensitivity comparable to single-stage enzymatic amplification may be obtained with reduced assay time.

The amplified active peroxidase formed by the association of the apo-enzyme and heme may be used in a variety of peroxide-driven detection methods such as immunoassays, detection of oligonucleotides, and nucleic acid hybridization techniques.

Sandwich-Type Reaction Exemplified Using Antibodies

In one aspect, the present methods may be employed using the blocked heme ester in a reaction scheme as follows. A capture-binder (e.g. an antibody) specific for the analyte of interest may be bound covalently or non-covalently (e.g., by adsorption) on to a solid support. The test sample may then be applied. The test sample may be in solution or may be in a form that solubilizes upon introduction into a liquid associated with the solid support. When the solid support is integrated into the reaction vessel, such as a well in a microtiter plate, the reaction solution is dispensed in the reaction vessel. When the solid support is a bead, a membrane, or some other detachable component, the solid support may be dispensed in a container along with the assay solution.

A label-binder, which may be the same or different as the capture-binder, is directly or indirectly conjugated to a choline esterase. The label-binder is added to the assay solution containing the bound analyte. Unbound sample components may be washed away and a solution of heme choline esters and inactive peroxidase is added. The choline esterase unblocks the heme choline esters to heme, which in turn converts apo-peroxidase to active peroxidase. Following addition of a peroxide and a peroxide-sensitive signal generator (e.g., TMB) signal develops in proportion to the amount of analyte captured by the capture-binder.

Samples

The sample tested in the provided assays may be of any source, for example a biological sample. A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., chimpanzee, or human).

Binders

In some embodiments, the analyte is attached to a solid support through a capture-binder that captures the analyte. Following analyte capture, the esterase is bound to the captured analyte using a label-binder.

In some embodiments, the esterase is conjugated directly to the label binder, for example using a primary anti-analyte antibody that is conjugated to the esterase. In other embodiments, the esterase is indirectly attached to the label binder, for example using a secondary antibody conjugated to the esterase that is reactive to the primary antibody. Other primary-secondary binder approaches may also be used, such as biotin-avidin and other art-recognized binding pairs.

Suitable binders may include one or more of natural or modified peptides, proteins (e.g., antibodies or affibodies), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the analytes available for detection. For example, an analyte in the sample may include a ligand and the binder may include a receptor or an analyte may include a receptor and the binder may include a ligand. Similarly, an analyte may include an antigen and the binder may include an antibody or antibody fragment or vice versa. In some embodiments, an analyte may include a nucleic acid and the binder may include another nucleic acid that is at least partially complementary. In some embodiments, both the analyte and the binder may include proteins capable of binding to each other.

Solid Supports

In assays using the compound of formula I, the analyte is adhered to a solid support, which may be any surface comprised of a porous or non-porous water insoluble material. In some embodiments, the end user performs that step of adhering the analyte or a capture binder for the analyte to the solid surface. The surface can have any one of a number of shapes, such as a plate, a well, a strip, a rod, a particle, or a bead. The surface can be hydrophilic or capable of being rendered hydrophilic and includes inorganic powders such as silica, magnesium sulfate, and alumina, natural polymeric materials, such as materials derived from cellulose, such as fiber containing papers (e.g., filter paper or chromatographic paper). The solid support may comprise synthetic or modified naturally occurring polymers, such as nitrocellulose, cellulose acetate, poly(vinyl chloride), polyacrylamide, dextran, agarose, polyacrylate, polyethylene, polypropylene, poly(4-methylbutene), polystyrene, polymethacrylate, poly(ethylene terephthalate), nylon, or poly(vinyl butyrate).

Choline Esterases

Choline esterases are used as first-stage enzymes to hydrolyze heme choline esters to the free heme. Typically the choline esterase introduced into the assay solution associated with a binder, which attaches to the previously bound analyte. After removing unbound material, a solution of heme choline esters and apo-peroxidase is added. The bound choline esterase hydrolyzes the heme choline esters forming heme, which in turn converts apo-peroxidase to active peroxidase. Following addition of peroxide and a peroxide-sensitive signal generator (e.g., TMB) a signal develops in proportion to the amount of analyte captured by the first binder.

As used herein, the term "choline esterase" refers to those enzymes that act on a variety of choline esters to hydrolyze an acylcholine forming choline and a carboxylate and is commonly referred to as choline esterase II (unspecific) and is classified according to the Enzyme Commission list of enzyme under EC number 3.1.1.8. It does not include acetylcholine esterase, which hydrolyzes acetylcholine forming choline and acetate and is commonly referred to as choline esterase I. Examples of choline esterase include acylcholine acylhydrolase, benzoylcholine esterase, butyrocholine esterase, choline esterase, butyrylcholine esterase, propionylcholine esterase, pseudocholine esterase, or serum choline esterase.

Heme Peroxidases

Heme peroxidase is used in the methods as the second stage enzyme that functions as a donor:hydrogen-peroxide oxidoreductase that contains heme as a cofactor.

Heme peroxidases are widespread in bacteria, fungi, plants and mammals and peroxidase-catalyzed oxidation of organic compounds is a common electron transfer process in molecular biology. Phenols and anilines are generally recognized as substrates of the heme peroxidases (donor: $H_2O_2$ oxidoreductases) whereby the peroxidases catalyze oxidation of the substrates by hydrogen peroxide or alkyl peroxides, usually but not always, via free-radical intermediates. Non-phenolic compounds, such as indole-3-acetic acid, phenylenediamines, ferrocenes, phenothiazines, phenoxazines, are also useful as peroxidase substrates.

Apo-peroxidase is added as a solution with the heme choline esters to the reaction chamber. Apo-peroxidases useful in the present invention include the apo forms of heme myeloperoxidase; lactoperoxidase; verdoperoxidase; guaiacol peroxidase; thiocyanate peroxidase; eosinophil peroxidase; Japanese radish peroxidase; horseradish peroxidase (HRP); extensin peroxidase; heme peroxidase; MPO; oxyperoxidase; protoheme peroxidase; pyrocatechol peroxidase; scopoletin peroxidase or cytochrome-c peroxidase.

Peroxide-Activated Signal Generators

In general, the peroxide-activated signal generators useful in the present methods include chromogenic substrates, colorimetric substrates, fluorogenic substrates, labeled tyramides, and chemiluminescent substrates.

Representative signal generators include 3,3',5,5'-tetramethylbenzidine (TMB); 3,3'-diaminobenzidine (DAB), 3-amino-9-ethylcarbazole (AEC) 2,2-azino-bis(3-ethylbenzthiazoline-6-sulfonic acid) (ABTS), o-phenylenediamine (OPD), o-dianisidine, 5-aminosalicylic acid, 4-chloro-1-naphthol. Representative fluorogenic substrates include, but are not limited to, homovanillic acid or 4-hydroxy-3-methoxyphenylacetic acid, reduced phenoxazines and reduced benzothiazines, including Amplex Red reagent and its variants (U.S. Pat. No. 4,384,042), Amplex UltraRed and its variants in (WO05042504) and reduced dihydroxanthenes, including dihydrofluoresceins (U.S. Pat. No. 6,162,931) and dihydrorhodamines including dihydrorhodamine 123. Representative chemiluminescent substrates include, but are not limited to, luminol, acridans, acridinium esters, and dioxetanes.

Signal Development

In some embodiments, the signal development involves the chemical modification of a signal generator to produce color, luminescence, or fluorescence (e.g., using TMB, luminal, or Amplex Red, respectively). In alternative embodiments, the signal development entails the localization of signal by modification causing the signal generator to bind at the region of its oxidation (e.g., tyramide deposition).

Standardization

In addition to the samples to be tested, a series of wells may be prepared using known concentrations of the analyte. A curve, plotting the optical density versus the concentration of analyte in these standard wells is prepared. By comparing the optical density of the samples to this standard curve, the concentration of the analyte in the unknown samples may then be determined.

Kits

Another aspect of the invention provides kits for the detection of a target analyte, wherein the kit comprises detection reagents for determining the presence of a target analyte in a peroxidase assay. Additional kit components may include a solid support, instructions to use the solid support, signal generators, buffers and standards. In one embodiment of the invention, the detection reagents include a butyrylcholine esterase-conjugated antibody reagent specific for the analyte to be tested and heme choline esters. The heme choline ester may be the heme mono or bis choline ester or a combination thereof.

The kits may further include various buffers for use in the inventive assays. These buffers include, but are not limited to, PBS, Tris, MOPS, HEPES, and phosphates allowing for control of pH. The pH will vary depending upon the particular assay system, generally within a readily determinable range. The concentration of buffer may be in the range of about 0.1 to 500 mM. Alternatively, the concentration of the buffer may be in the range of 0.5 to 200 mM.

The kit reagent may be provided in solution form for ease of handling. Alternatively, one or more reagents may be lyophilized to preserve activity and extend shelf life. Additionally, compatible reagents (e.g., signal generator, buffer, and peroxide) may be combined in solution at concentrations that enable facile use of the kit components.

EXAMPLES

Practice of the invention will be still more fully understood from the following examples, which are presented herein for illustration only and should not be construed as limiting the invention in any way.

The following synthetic method, as shown in Reaction Scheme 1, was used for the production and isolation of heme choline esters.

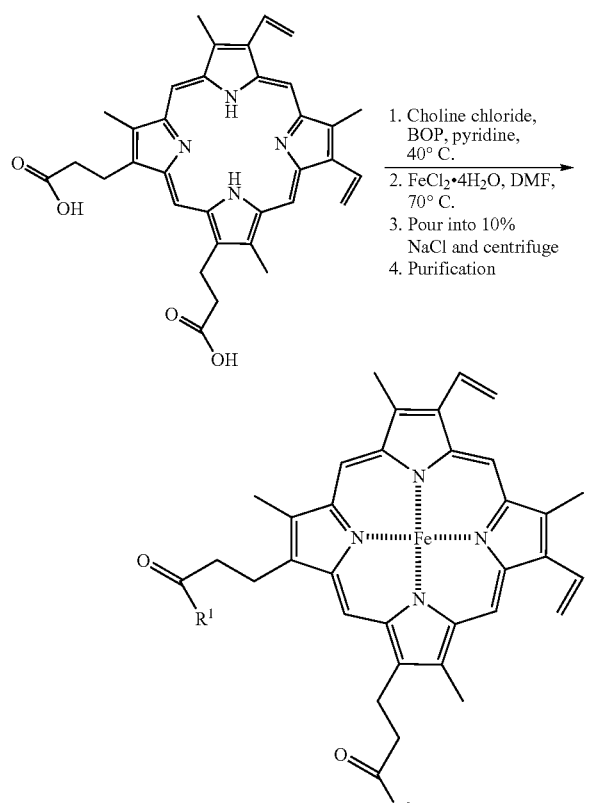

Reaction Scheme 1

1. Choline chloride, BOP, pyridine, 40° C.
2. FeCl$_2$·4H$_2$O, DMF, 70° C.
3. Pour into 10% NaCl and centrifuge
4. Purification wherein R$^1$ and R$^2$ are as defined above for formula I A mixture of protoporphyrin IX (52 mg, 0.092 mmol), choline chloride (64 mg, 0.462 mmol, 5 eq.) and (benzotriazol-1-yloxy)tris(dimethylamino)phosphonium hexafluorophosphate (0.204 g, 0.462 mmol, 5 eq.) in pyridine (1 mL) was heated to 40° C. under nitrogen and stirred for 6 h, then cooled to room temperature. To this mixture was added iron (II) chloride tetrahydrate (0.190 g, 0.956 mmol, 10 eq.) and N,N-dimethylformamide (1 mL) and this mixture was heated at 70° C. for 5 h, then cooled to room temperature. The reaction mixture was poured into 10% aqueous sodium chloride at 5° C. and was centrifuged at 3500 rpm for 15 minutes and placed in the refrigerator overnight. The supernatant was removed and the residual material was lyophilized, which provided a mixture of mono and bis choline esters. This mixture was subjected to preparative reverse phase HPLC (Phenomenex Gemini 5 μm C18, 30×100 mm), which afforded the mono and bis choline ester: mono ester: UV lambda max=398 nm; LRMS-(MALDI+) calcd for ($C_{39}H_{44}FeN_5O_4$) [M]$^+$ 702.27, found 702.30; bis ester: UV lambda max=398 nm; LRMS-(ESI+) calcd for ($C_{44}H_{56}FeN_6O_4$) [M/2]$^+$ 394.18, found 394.16.

Example 2

Hydrolysis of Heme Bis Choline Ester Shown by HPLC

To confirm enzymatic hydrolysis of heme bis choline ester, a sample of bis choline ester in methanol was added to a solution of butyrylcholine esterase (BCE) (50 units) in phosphate buffer (pH 7.0). The progress of the hydrolysis was determined by HPLC analysis of the reaction mixture using a Waters Xterra C18 reverse phase column (4.6×50 mm). A gradient elution was performed starting with 95:5 water (+0.1% TFA):acetonitrile (+0.1% TFA) up to 0:100 over 10 minutes followed by isocratic elution with acetonitrile (+0.1% TFA) for 5 minutes. The flow rate was 1 mL/min and the samples were observed at 400 nm. Under these conditions the bis ester elutes first (tR=5.2 min) followed by the monoester (5.9 min) and heme (6.6 min). The Hydrolysis vs. Time, converted to concentration and reported as AUC units is provided in Table 1.

TABLE 1

|  | 0 hr | 0.75 hr | 2.75 hr | 21 hr |
| --- | --- | --- | --- | --- |
| Bis ester | 100 | 60 | 52 | 41 |
| Mono ester | NA | 28 | 29 | 24 |
| Heme | NA | 7 | 12 | 21 |

Example 3

Signal Enhancement from HRP-Based Cascade Using a Chromogenic Substrate

Apo-HRP in combination with butyrylcholine esterase (BCE) and blocked heme demonstrated a stronger signal relative to conventional single-stage amplification using horseradish peroxidase. A 15-fold enhancement in peroxidase signal was calculated from the samples and data in Table 2.

TABLE 2

| Sample | BCE | Apo-horseradish peroxidase | Blocked Heme | Horseradish peroxidase | OD 650 nm |
|---|---|---|---|---|---|
| A1 | 0.7 fmol | 12 pmol | 250 fmol | 0 | 1.05 |
| B1 | 7 fmol | 12 pmol | 0 | 0 | 0.04 |
| A2 | 0 | 0 | 0 | 0.7 fmol | 0.10 |
| B2 | 0 | 12 pmol | 250 fmol | 0 | 0.16 |

The samples in Table 2 were prepared from the following stock solutions. A 120 µM stock solution of apo-HRP was prepared by adding 2 mL phosphate-buffered saline (PBS, Pierce 28372) to 10 mg lyophilized apo-HRP (Sigma 6278, MW=43000 g/mol). A 250 µM stock solution of horseradish peroxidase type VI (HRP, Sigma P8375, MW=44000 g/mol) was prepared by solubilizing 11 mg lyophilized protein in 1 mL 100 mM sodium phosphate, pH 7.0. A 1 kU/mL stock solution of butyrylcholine esterase was prepared by dissolving 1 kU lyophilized protein (Sigma C1057) in 1 mL phosphate-buffered saline (PBS, Pierce 28372). Assuming an activity of 900 U per mg protein and MW=250000 g/mol, the concentration of the resultant solution was estimated as 4 µM. Less than 1 mg heme bis choline ester was dissolved in 100 µL methanol. 10 µL of this methanol solution was then mixed with 90 µL of 100 mM borate buffer, pH 9.1. The 1 cm-path length absorbance of this 10% methanol solution was measured to be 17 absorbance units (au) at 390 nm using a Nano-Drop-1000 Spectrophotometer. Assuming an extinction coefficient at 390 nm equivalent to that of heme (approximately 40 $cm^{-1}$ $mM^{-1}$), a 0.1 mM stock solution of the heme bis choline ester was then prepared by mixing 23.5 µL of the 10% methanol solution with 77.5 µL PBS.

Solutions of 0.13 nM HRP, 1 µM heme bis choline ester and 4.4 nM butyrylcholine esterase were prepared by dilution of these stock solutions with PBS. The reaction mixtures in Table 2 were then prepared in the following manner:

(A1) 10 µL of 120 µM apo-HRP was first mixed with 15 µL of 4.4 nM butyrylcholine esterase, and then 25 µL of 1 µM heme bis choline ester was added. The solution was allowed to sit for 16 hours at room temperature. 5 µL of a ten-fold dilution of this reaction was used as sample.

(B1) 10 µL of 120 µM apo-HRP was first mixed with 15 µL of 4.4 nM butyrylcholine esterase, and then 25 µL PBS was added. The solution was allowed to sit for 16 hours at room temperature. 5 µL of a ten-fold dilution of this reaction was used as sample.

(A2) 5 µL of 0.13 nM HRP was used as sample.

(B2) 10 µL of 120 µM apo-HRP was first mixed with 15 µL PBS, and then 25 µL of 1 µM heme bis choline ester was added. The solution was allowed to sit for 16 hours at room temperature. 5 µL of a ten-fold dilution of this reaction was used as sample.

Samples A1, A2, B1, and B2 were each combined with 95 µL 3,3',5,5'-tetramethylbenzidine (TMB) liquid substrate system (Sigma T8665), which includes hydrogen peroxide. After 6 minutes OD was determined at 650 nm in a 96-well format using a SpectraMax M2 plate reader (Molecular Devices). These signals are recorded in Table 2 above.

Relative signal enhancement was calculated by subtracting appropriate background signals from wells A1 and A2, and then taking a ratio. The absorbance of sample A1 was corrected for the peroxidase activity of sample without butyrylcholine esterase (sample B2) and the absorbance of sample A2 was corrected for transmitted light that is intrinsically lost to reflective interfaces during measurement. For example, the signal observed for sample B1 is due almost entirely to such losses. The calculated signal enhancement is thus equal to (A1−B2)/(A2−B1), which corresponds to (1.05−0.16)/(0.10−0.04)=15. As the molar concentration of butyrylcholine esterase in sample A1 is the same as the molar concentration of HRP in sample A2 the two-stage cascade (blocked peroxidase activity rescued by butyrylcholine esterase) generates more signal per unit of first-stage enzyme than a conventional, one-stage signal amplification scheme using only HRP.

Example 4

Signal Enhancement from HRP-Based Cascade Using a Chemiluminescent Substrate

Apo-HRP in combination with butyrylcholine esterase (BCE) and blocked heme demonstrated a stronger signal relative to conventional single-stage amplification using horseradish peroxidase. A 34-fold enhancement in peroxidase signal was calculated from the samples and data in Table 3.

TABLE 3

| Sample | BCE | Apo-HRP | Blocked Heme | Horseradish peroxidase | LU |
|---|---|---|---|---|---|
| A3 | 0.7 fmol | 12 pmol | 250 fmol | 0 | 202,200 |
| B3 | 0 | 12 pmol | 250 fmol | 0 | 133,700 |
| A4 | 0 | 0 | 0 | 0.7 fmol | 2,300 |
| B4 | 0 | 0 | 0 | 0 | 300 |

Solutions of 0.13 nM HRP, 1 µM heme bis choline ester and 0.44 nM BCE were prepared as described above. The reaction mixtures in Table 3 were then prepared in the following manner:

(A3) 10 µL of 120 µM apo-HRP was first mixed with 15 µL of 0.44 nM butyrylcholine esterase, and then 25 µL of 1 µM heme bis choline ester was added. The solution was allowed to sit for 34 hours at room temperature. 5 µL of this reaction was used as sample.

(B3) 10 µL of 120 µM apo-HRP was first mixed with 15 µL PBS, and then 25 µL of 1 µM heme bis choline ester was added. The solution was allowed to sit for 34 hours at room temperature. 5 µL of this reaction was used as sample.

(A4) 5 µL of 0.13 nM HRP was used as sample.

(B4) 5 µL PBS was used as sample.

Luminescence units were acquired with a SpectraMax M5 plate reader in a 96-well format (Molecular Devices) 6 minutes after 95 µL of freshly mixed chemiluminescent substrate (Sigma CPS260) was added to each of the samples. The LUs measured for sample B3 are a background signal that arises from the incomplete blocking of peroxidase activity in mixtures of apo-HRP and heme bis choline ester. The LUs measured for sample B4 are an intrinsic background signal for the luminometer.

Referring to Table 3 sample A3 results in 202,200 LUs compared to sample A4, which results in 2,300 luminescent units. Correcting samples A3 and A4 for background luminescence (samples B3 and B4, respectively) gives a 34-fold signal enhancement using the following formula: (A3−B3)/(A4−B4)=34. Accordingly, since the molar concentration of butyrylcholine esterase in sample A3 is equivalent to the molar concentration of HRP in sample A4, the data demonstrates a two-stage enzymatic cascade (blocked peroxidase activity rescued by butyrylcholine esterase) generates more signal per unit of first-stage enzyme than conventional, one-stage signal amplification (the intrinsic peroxidase activity of HRP).

Example 5

Recombination of Heme and Apo-HRP for Signal Amplification

A 250 µM stock solution of horseradish peroxidase type VI (HRP, Sigma P8375, MW=44000 g/mol) was prepared by solubilizing 11 mg of lyophilized protein in 1 mL 100 mM sodium phosphate, pH 7.0.

Heme was extracted from horseradish peroxidase type VI (Sigma P8375) according to the method of Teale (Biochim. Biophys. Acta 35, 543, (1959)). The resultant apo-HRP was dialyzed into 100 mM sodium phosphate, pH 7.0, with 0.1 mM calcium chloride. The concentration of this stock apo-HRP solution was estimated from absorbance at 280 nm as 30 µM by assuming an extinction coefficient of 20000 cm$^{-1}$ M$^{-1}$ (Lasagna et al., Biophys. J. 76, 443, (1999)).

Within an hour before performing the peroxidase assay a fresh stock solution of approximately 1 mM heme (MW 652 g/mol) was prepared by first dissolving 38.9 mg heme (Sigma H5533) in 1 mL of 1.0M NaOH and then mixing 100 µL of the resulting solution with 6 mL 100 mM borate buffer, pH 9.1.

The absorbance data in Table 4 was acquired using a SpectraMax M2 plate reader (Molecular Devices) in 96-sample format. The HRP stock solution was diluted serially with 100 mM sodium phosphate, pH 7.0, to make 2000, 500 and 50 pM solutions. 10 µL of each solution was then mixed with 90 µL 3,3',5,5'-tetramethylbenzidine (TMB) liquid substrate system (Sigma T8665) to define t=0. The absorbance at 650 nm was measured after 30 min and corrected for the absorbance of TMB solution without added HRP.

The heme stock solution was diluted serially with 100 mM borate buffer, pH 9.1, to make 2000 pM, 500 pM, and 50 pM solutions. 10 µL of each solution was first mixed with 1 µL of the apo-HRP stock solution and then immediately mixed with 90 µL TMB liquid substrate system to define t=0. The absorbance at 650 nm was measured after 30 min and corrected for the absorbance of a mixture of apo-HRP and TMB liquid substrate system without added heme.

The colorimetry measurements in Table 4 demonstrate the activation of apo-HRP by heme. At t=30 minutes, a solution of 20 fmol heme and 30 pmol apo-HRP gives signal comparable to 5 fmol HRP.

TABLE 4

| Sample | OD 650 nm |
|---|---|
| 20 fmol heme, 30 pmol apo-horseradish peroxidase | 0.79 |
| 20 fmol horseradish peroxidase | 3.4 |
| 5 fmol heme, 30 pmol apo-horseradish peroxidase | 0.07 |
| 5 fmol horseradish peroxidase | 0.88 |

Example 6

Blocking and Rescue of Peroxidase Activity Demonstrated with a Chemiluminescent Substrate A 1-kU/mL stock solution of butyrylcholine esterase was prepared by dissolving 1 kU of lyophilized protein (Sigma C1057) in 1 mL phosphate-buffered saline (PBS, Pierce 28372). An activity of 900 U per mg protein and MW=250000 g/mol was assumed and the concentration of the resultant solution was estimated as 4 µM.

A 1 kU/mL stock solution of acetylcholine esterase was prepared by dissolving 1 kU lyophilized protein (Sigma C2888) in 1 mL phosphate-buffered saline (PBS, Pierce 28372). An activity of 1000 U per mg protein and MW=280000 g/mol was assumed and the concentration of the resultant solution was estimated as 4 µM.

A fresh 1 mM solution of heme was prepared in 100 mM borate buffer, pH 9.1, as described in Example 5. The 1 cm-path length absorbance of this solution was measured to be 40 at 390 nm using a NanoDrop-1000 Spectrophotometer (NanoDrop Technologies). A 0.1 mM heme solution was then prepared by mixing 100 µL of this stock with 900 µL in PBS.

Less than 1 mg heme bis choline ester was dissolved in 100 µL methanol. 10 µL of the methanol solution was then mixed with 90 µL 100 mM borate buffer, pH 9.1. The 1 cm-path length absorbance of this 10% methanol solution was measured to be 17 absorbance units (au) at 390 nm using a NanoDrop-1000 Spectrophotometer. Assuming the extinction coefficient of heme bis choline ester in 10% methanol was not substantially different than that of heme in PBS, a 0.1 mM solution of heme bis choline ester was then prepared by mixing 23.5 µL of the 10% methanol solution with 77.5 µL PBS.

Solutions of 0.3 µM apo-HRP, 10 µM heme and 10 µM heme bis choline ester in PBS were prepared by dilution of these stock solutions with PBS.

Data in Table 5 refers to the following samples:
(1) 5 µL 3 nM apo-HRP+5 µL 1 µM heme bis choline ester+5 µL PBS.
(2) 5 µL 3 nM apo-HRP+5 µL 1 µM heme bis choline ester+5 µL 4 µM acetylcholine esterase.
(3) 5 µL 3 nM apo-HRP+5 µL 1 µM heme bis choline ester+5 µL 4 µM butyrylcholine esterase.
(4) 5 µL 3 nM apo-HRP+5 µL 0.1 µM heme+5 µL PBS.
(5) 5 µL 3 nM apo-HRP+5 µL PBS+5 µL 4 µM butyrylcholine esterase.
(6) 5 µL 3 nM apo-HRP+10 µL PBS.

90 µL of freshly mixed chemiluminescent substrate (Sigma CPS260, an enhanced luminol product with a stabilized peroxide buffer solution) was added to reaction mixtures 1-6, which were allowed to incubate at room temperature for 5 minutes and the luminescence units (LU) for each was determined with a SpectraMax M2 plate reader in a 96-well format (Molecular Devices), shown below in Table 5.

TABLE 5

| Sample | LU |
|---|---|
| 1 | 580 |
| 2 | 450 |
| 3 | 3200 |
| 4 | 3900 |
| 5 | 710 |
| 6 | 190 |

The data shown in Table 5 demonstrate that horseradish peroxidase activity is rescued by addition of BCE, which enzymatically converts heme bis choline ester to both heme mono choline ester and free heme. The larger LU value for sample 3 compared with samples 1 and 5 demonstrates that the rescue of peroxidase activity is specific to the combination of BCE and its blocked heme substrate, heme bis choline ester. When either of these components was missing from a reaction mixture, as was the case for samples 1 and 5, less peroxidase activity is observed. The smaller LU value for sample 2 compared with sample 3 illustrates that the rescue of peroxidase activity is specific to the action of BCE; an alternative enzyme, acetylcholine esterase, did not demonstrably rescue peroxidase activity. The small LU value shown in sample 5 may be attributed to trace components present in the naturally occurring lyophilized protein used to prepare the BCE stock solution. The non-zero LU value for sample 6 may be attributed to small background level of peroxidase activity from reactions containing only apo-HRP.

The lower LU value for sample 1 compared with sample 4, despite the 10-fold excess of heme bis choline ester in sample 1 compared with the heme in sample 4, illustrates that mixtures of apo-HRP and heme bis choline ester exhibit less peroxidase activity than equivalent mixtures of apo-HRP and heme.

Equivalents

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

We claim:

1. A method of detecting the presence of an analyte in a sample comprising the steps of:
   (a) providing a first binder capable of specifically binding the analyte, wherein the first binder is attached to a solid surface;
   (b) applying the sample to the solid surface under conditions that permit the first binder to bind to analyte present in the sample;
   (c) adding a second binder, wherein the second binder comprises a conjugate comprising a binder portion that binds to the analyte captured by the first binder and a choline esterase;
   (d) adding an apo-peroxidase, a heme choline ester, a peroxide, and a peroxide-activated signal generator; and
   (e) detecting the signal produced by the peroxide-activated signal generator.

2. The method of claim 1, wherein the heme choline ester comprises a heme mono choline ester, a heme bis choline ester, or combinations thereof.

3. The method of claim 1, wherein the heme choline ester comprises the compound of formula I:

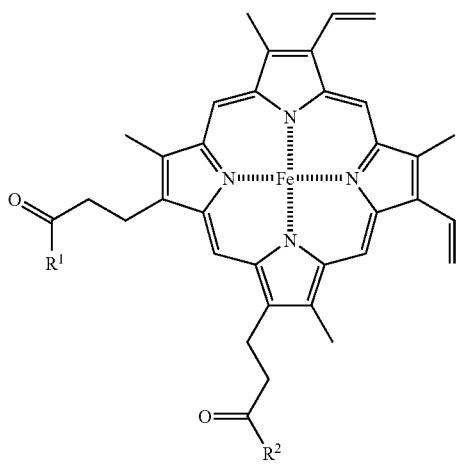

wherein $R^1$ and $R^2$ are choline or hydroxyl; or $R^1$ and $R^2$ are choline;

with the proviso that $R^1$ and $R^2$ are not both hydroxyl.

4. The method of claim 1, further comprising a washing step after step (c).

5. The method of claim 1, wherein the binder portion of the second binder which binds to the analyte captured by the first binder comprises an antibody, an affibody, an aptamer, a nucleic acid probe, a polysaccharide, a lipid, an enzyme, an enzyme substrate, a ligand, or a receptor that specifically binds to the analyte.

6. The method of claim 1, wherein the apo-peroxidase is selected from the apo form of heme myeloperoxidase; lactoperoxidase; verdoperoxidase; guaiacol peroxidase; thiocyanate peroxidase; eosinophil peroxidase; Japanese radish peroxidase; horseradish peroxidase (HRP); soybean peroxidase; extensin peroxidase; heme peroxidase; MPO; oxyperoxidase; protoheme peroxidase; pyrocatechol peroxidase; scopoletin peroxidase, or cytochrome-c peroxidase.

7. The method of claim 1 wherein the choline esterase is butyrylcholine esterase.

8. The method of claim 1, further comprising performing steps (a)-(e) on a positive control sample.

9. The method of claim 1, wherein the solid surface is covered with a solution.

10. The method of claim 1, wherein the sample comprises a solid that is solubilized in a solution covering the solid support.

11. The method of claim 1, wherein the peroxide comprises hydrogen peroxide.

12. The method of claim 1, wherein the peroxide-activated signal generator comprises a 3,3',5,5'-tetramethylbenzidine (TMB), an aminophthalhydrazide, an acridan, an acridinium ester, a dioxetane, a luminol, a 2,2'-azinodi(3-ethylbenzthiazoline sulfonic acid) (ABTS), a 3,3'-diaminobenzidine (DAB), a tyramide, a labeled phenol, or a 3-amino-9-ethylcarbzole (AEC).

13. The method of claim 1, wherein the solid support comprises nitrocellulose, cellulose acetate, poly(vinyl chloride), polyacrylamide, dextran, agarose, polyacrylate, polyethylene, polypropylene, poly(4-methylbutene), polystyrene, polymethacrylate, poly(ethylene terephthalate), nylon, or poly(vinyl butyrate).

14. The method of claim 1, wherein the detection step comprises determining the optical density, fluorescent intensity, or luminosity of the signal generator associated with the bound analyte.

15. The method of claim 14, further comprising correlating the optical density, fluorescent intensity, or luminosity of the signal generator associated with the bound analyte to the concentration of the analyte in the sample.

16. The method of claim 1, wherein the detection step comprises visual inspection of the signal produced in step (e).

* * * * *